(12) United States Patent
Traneus

(10) Patent No.: US 12,090,344 B2
(45) Date of Patent: Sep. 17, 2024

(54) RADIATION MODULATOR ASSEMBLY AND RADIATION DELIVERY APPARATUS FOR USE IN ION-BASED RADIOTHERAPY AND A PLANNING METHOD FOR ION-BASED RADIOTHERAPY

(71) Applicant: RaySearch Laboratories AB (Publ), Stockholm (SE)

(72) Inventor: Erik Traneus, Uppsala (SE)

(*) Notice: Subject to any disclaimer, the term of this patent is extended or adjusted under 35 U.S.C. 154(b) by 0 days.

(21) Appl. No.: 18/262,920

(22) PCT Filed: Feb. 3, 2022

(86) PCT No.: PCT/EP2022/052589
§ 371 (c)(1),
(2) Date: Jul. 26, 2023

(87) PCT Pub. No.: WO2022/167528
PCT Pub. Date: Aug. 11, 2022

(65) Prior Publication Data
US 2024/0033540 A1    Feb. 1, 2024

(30) Foreign Application Priority Data
Feb. 8, 2021 (EP) .................................... 21155682

(51) Int. Cl.
*A61N 5/10* (2006.01)

(52) U.S. Cl.
CPC ......... *A61N 5/1081* (2013.01); *A61N 5/1031* (2013.01); *A61N 2005/1087* (2013.01); *A61N 2005/1095* (2013.01)

(58) Field of Classification Search
CPC .............. A61N 5/1081; A61N 5/1031; A61N 2005/1087; A61N 2005/1095
See application file for complete search history.

(56) References Cited

U.S. PATENT DOCUMENTS 6,034,377 A * 3/2000 Pu ........................... G21K 5/10
                                                                250/398
7,977,656 B2 * 7/2011 Fujimaki ................ G21K 1/043
                                                                378/65
(Continued)

FOREIGN PATENT DOCUMENTS

CN    102596316 A    7/2012
JP    2000176028 A    6/2000
(Continued)

OTHER PUBLICATIONS

Vozenin et al.: The advantage of FLASH radiotherapy confirmed in mini-pig and cat-cancer patients, HAL Id: hal-01812514, https://hal-univ-rennes1.archives-ouvertes.fr/hal-01812514v2.
(Continued)

*Primary Examiner* — David A Vanore
(74) *Attorney, Agent, or Firm* — Noréns Patentbyrå AB

(57) ABSTRACT

A radiation delivery system includes a chair on which the patient may be seated during treatment and a modulating assembly (10) for use in radiotherapy comprises a modulator wheel (15), said modulator wheel being shaped as a rim defining the circumference of a circle or an elliptic shape, and having varying thickness around the circumference, said modulator wheel (15) being arranged in such a way that a beam traveling from a radiation source (13) to a patient will intersect the rim of the modulator wheel, said wheel being arranged to rotate in such a way that the beam will intersect the rim in varying positions around the circumference. The wheel will modulate the energy of the beams passing through material having varying thickness as the modulator wheel rotates.

11 Claims, 3 Drawing Sheets

(56) References Cited

U.S. PATENT DOCUMENTS

| | | | |
|---|---|---|---|
| 11,141,608 B2* | 10/2021 | Cavuto | G21K 1/10 |
| 11,517,767 B2* | 12/2022 | Bokrantz | A61N 5/1043 |
| 11,636,594 B2* | 4/2023 | Svensson | A61B 5/055 |
| | | | 382/131 |
| 11,786,753 B2* | 10/2023 | Traneus | A61N 5/1043 |
| | | | 600/1 |
| 2005/0051740 A1* | 3/2005 | Yanagisawa | A61B 90/96 |
| | | | 250/492.1 |
| 2009/0299634 A1* | 12/2009 | Schaffner | A61N 5/1048 |
| | | | 250/281 |
| 2010/0012859 A1* | 1/2010 | Claereboudt | A61N 5/1043 |
| | | | 250/492.3 |
| 2014/0094643 A1* | 4/2014 | Gall | A61N 1/44 |
| | | | 600/1 |
| 2015/0099918 A1* | 4/2015 | Takayanagi | A61N 5/1071 |
| | | | 702/89 |
| 2015/0293235 A1* | 10/2015 | Cameron | G01T 1/023 |
| | | | 250/361 R |
| 2019/0022411 A1* | 1/2019 | Parry | A61K 31/436 |
| 2020/0094076 A1* | 3/2020 | Cavuto | G21K 5/04 |
| 2020/0246633 A1 | 8/2020 | Zamenhof | |
| 2021/0228906 A1* | 7/2021 | Traneus | A61N 5/103 |
| 2022/0040500 A1* | 2/2022 | Fredriksson | A61N 5/1078 |
| 2022/0296925 A1* | 9/2022 | Wedenberg | A61N 5/1031 |

FOREIGN PATENT DOCUMENTS

| | | |
|---|---|---|
| JP | 2003534066 A | 11/2003 |
| JP | 3751440 B2 | 3/2006 |
| JP | 2015530194 A | 4/2014 |
| JP | 2015097683 A | 5/2015 |
| JP | 2016105844 A | 6/2016 |
| WO | 2018187680 A1 | 10/2018 |

OTHER PUBLICATIONS

International Search Report and Written Opinion dated Apr. 28, 2022, European Patent Office, Rijswijk, Netherlands.
Office Action dated Dec. 21, 2023 in corresponding Japanese application No. 2023-541932, Tokyo, Japan.
Extended European search report dated Jul. 13, 2021, European Patent Office, Munich, Germany.
First Chinese office actiond dated Dec. 5, 2023, China.
Second Chinese office action dated Mar. 30, 2024, China.

* cited by examiner

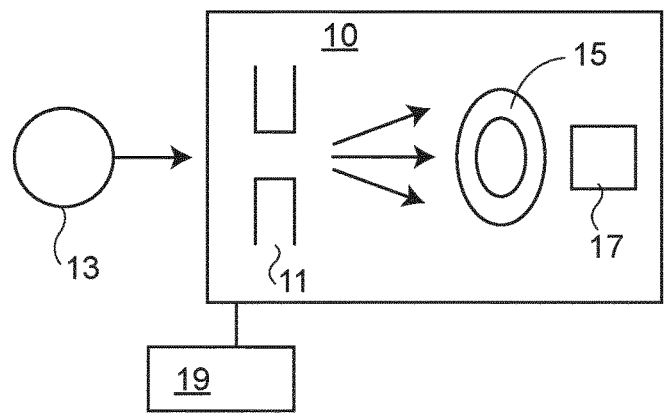
FIGURE 1a
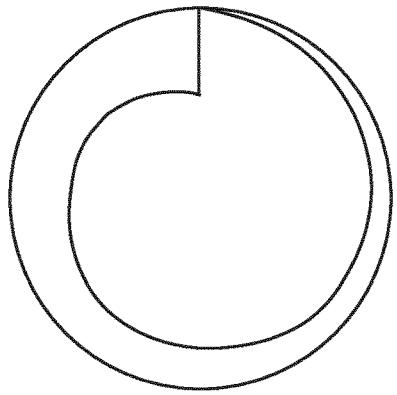 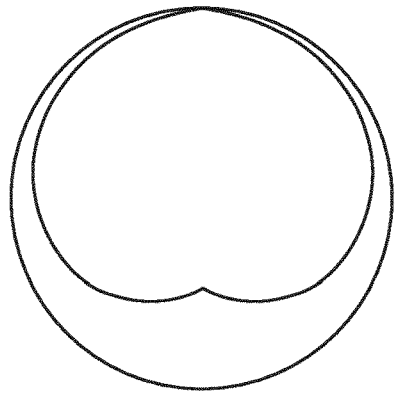
FIGURE 1b  FIGURE 1c
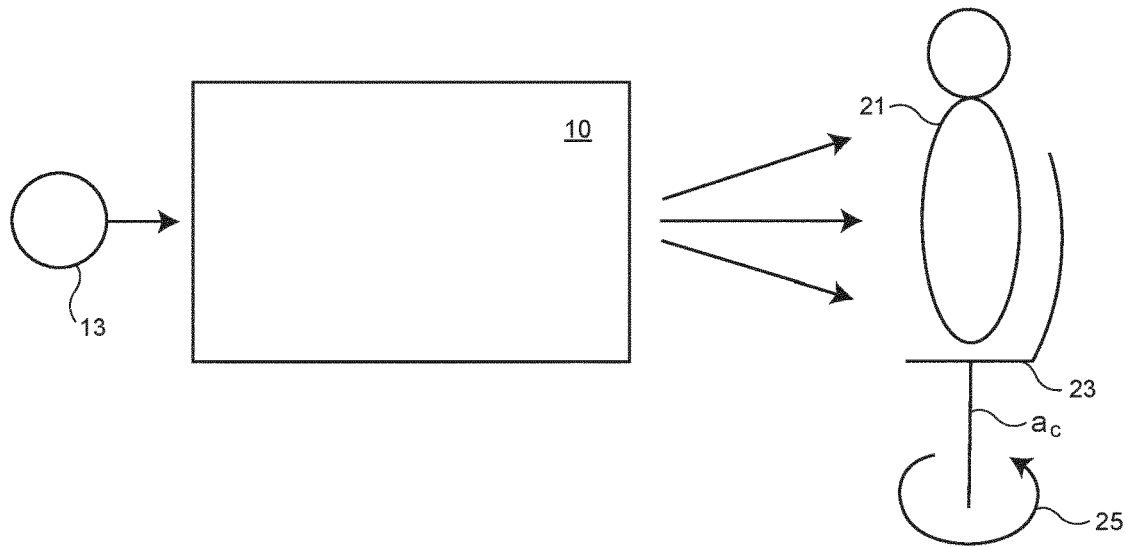
FIGURE 2a

RADIATION MODULATOR ASSEMBLY AND RADIATION DELIVERY APPARATUS FOR USE IN ION-BASED RADIOTHERAPY AND A PLANNING METHOD FOR ION-BASED RADIOTHERAPY

TECHNICAL FIELD

The present invention relates to a device for use in ion-based radiotherapy treatment and in particular to methods in which the dose is delivered by pencil beam scanning, and a system utilizing such a device. The invention also relates to a method of creating a delivery plan for use in such a system.

BACKGROUND

In pencil beam scanning, beams of protons, or other ions, are delivered to a patient in a scanning pattern. The beams include a number of energy layers for reaching different depths of the target, each layer including a number of spots distributed laterally over the target. In this way, the dose can be distributed as desired over the whole target in three dimensions. The delivery of each spot within an energy layer is fast but changing between energy layers is relatively slow, typically requiring between 0.3 and 1 second. Several planning methods therefore focus on reducing the number of energy layers, to enable efficient delivery of the plan.

This applies, in particular, to arc therapy, in which a target volume is irradiated from a range of directions, usually defined by an arc segment with its central point inside the target volume. The use of several energy layers from each of the different directions can cause the delivery times to be longer than what is practical.

The delivery time is also a limiting factor in FLASH therapy. FLASH therapy involves delivering dose at high dose rates under short time intervals, which has been found to have advantageous effects in terms of less damage to healthy tissue with unchanged tumorous tissue response. The short time intervals required for FLASH therapy mean that the delay caused an energy layer change will hamper the FLASH effect.

Vozenin et al.: The advantage of FLASH radiotherapy confirmed in mini-pig and cat-cancer patients, HAL Id: hal-01812514, https://hal-univ-rennes1.archives-ouvertes.fr/hal-01812514v2 confirmed that the differential effect between normal tissue and tumor subjected to FLASH therapy, that had previously been shown for mice, could also be seen in pigs and cats. Published US patent application No. 2019/0022411 also relates to FLASH therapy, which is said to give reduced side effects for the same dose. Dose rates of 40 Gy/s or more, up to more than 500 Gy/s are mentioned, allowing a dose fraction to be delivered in a fraction of a second.

A somewhat different approach is grid therapy, in which a high dose, for example 15 or 20 Gy, is given in the shape of a grid, in one or few fractions. In other words, a spatially fractionated dose distribution is achieved. The grid may be achieved by means of geometrically spaced pencil beams, or by using an aperture block with a pattern of through holes that will let through a number of geometrically spaced beams. It has been known for a while that this form of treatment reduces the damage to the skin, since the unaffected portions of the skin between the beams will help the damaged portions to heal. Grid therapy can be used with photon therapy or with charged particles, such as protons. For protons, the grid can be arranged by using physical collimators having slits or holes to divide the beam. Alternatively, a suitable pattern of uncollimated pencil beams may be applied.

It is an object of the present invention to enable faster delivery of a beam with multiple energy layers to a patient, in particular but not exclusively for use with arc therapy. Embodiments of the invention are particularly suitable for a combination of arc therapy with grid or FLASH therapy.

SUMMARY OF THE INVENTION

The invention relates to a radiation delivery apparatus comprising a radiation modulating assembly comprising a modulator wheel, said modulator wheel being shaped as a rim defining the circumference of a circle or an elliptic shape, and having varying thickness around the circumference, said modulator wheel being arranged in such a way that a beam traveling from a radiation source to a patient will intersect the rim of the modulator wheel, wherein the modulator wheel is arranged to rotate so that the beam will intersect the rim in varying positions around the circumference. The apparatus further comprises a support arranged to hold a patient during treatment, wherein the support is a chair in which the patient may be seated during treatment, said chair being arranged to rotate around a first axis so that during treatment the beam will enter the patient from different angles in a horizontal plane In this way, the beam energies will be modulated as the beam passes through material having varying thickness as the modulator wheel rotates and the modulated beam will enter the patient from different angles.

The radiation modulating assembly may further comprise a deflecting device arranged upstream of the modulator wheel, said deflecting device being arranged to deflect the beam in at least one dimension, in such a way that the deflected beam will intersect the rim of the modulator wheel. In some embodiments the deflecting device comprises a magnet such as a dipole magnet arranged to deflect the beam. Instead of a magnet, another arrangement for creating a magnetic field may be used.

The use of a deflection device for bending the beam enables the arrangement of spots in a fan pattern using only a single magnet with a narrow pole gap. This contributes to a very light and compact device an also allows for very fast spot scanning back and forth along the scan line. Preferably, the beam is deflected in one dimension perpendicular to the relative movement of the beam across the patient's body.

The combination of the relative rotation of the beam around the patient and a deflection device moving the beam in a direction having a component perpendicular to the direction of the rotation means that a single pencil beam can be deflected at varying angles to cover a wider area of the patient while also covering the patient from different rotation. Preferably, the deflection is perpendicular to the rotation. Typically, the rotation will cause the beam to cover all or a portion of the patient's circumference and the deflection will cause the beam to cover a larger vertical area of the patient.

This enables ARC therapy with multiple energy layers without slowing down the delivery. This simplifies the planning process since there is no need for energy layer considerations, which are a time consuming factor.

This also enables efficient FLASH therapy combined with ARC therapy with a pencil beam, if the radiation source is able to provide radiation at sufficiently high dose rates. This is particularly beneficial in risk organs. The effect is enhanced if a discrete set of chair angles are used and spaced so that there are low dose gaps between neighboring chair angles in the organs at risk.

The set up according to embodiments of the invention also enables the combination of ARC therapy with grid therapy.

The modulator wheel may be arranged in any suitable manner. For example, with a slanted orientation relative to the deflecting device, in such a way that a beam after passing through the deflecting device will intersect the rim once. It may also be arranged in such a way that a beam after passing through the deflecting device will intersect the rim twice and pass through the interior of the rim inbetween.

The radiation modulating assembly may further comprise a radiation source arranged to provide a static beam in such a direction that it will be deflected by the deflecting device and pass through the modulator wheel. Alternatively, the radiation source may be arranged separately from the radiation modulating assembly.

The radiation modulating assembly according to any one of the preceding claims may further comprise an aperture device downstream of the modulator wheel. This aperture device may be any type of static or adjustable aperture device known in the art.

The chair may further be rotatably mounted on a rotatable base plate arranged to rotate around a second axis during treatment. The chair in this case is mounted so that the first axis is spaced apart from the second axis in the horizontal plane. This enables a more complex movement of the patient, allowing the radiation to be delivered in more complex patterns, for example, including concave shapes. The same effect can also be achieved by linearly displacing the chair along two axes, typically two perpendicular axes.

Alternatively, the support may be a couch, on which the patient can lay down in the conventional way, the device comprising a gantry, wherein the gantry includes the radiation source and the deflecting device.

Aspects of the invention also relate to a computer-implemented method of optimizing a radiotherapy treatment plan for providing treatment to a patient, wherein the optimization is performed using an treatment plan optimization problem and a model of a treatment apparatus as discussed above. The treatment plan optimization problem is setup by defining goals (objective functions) for target dose coverage and risk organ protection from too high doses. In addition, goals for plan robustness and for example LET and variable RBE dose objectives can be considered. If delivery is under FLASH conditions or GRID conditions objectives of relevance for FLASH therapy and GRID therapy effects can be considered.

BRIEF DESCRIPTION OF DRAWINGS

The invention will be described in more detail in the following, by way of examples and with reference to the appended drawings.

FIG. 1a illustrates a modulating device according to embodiments of the invention and FIGS. 1b and 1c illustrate alternative shapes of the modulator wheel which is part of the modulating device.

FIGS. 2a, 2b and 3 disclose embodiments of a radiotherapy treatment apparatus including a modulating device according to FIG. 1a.

DETAILED DESCRIPTION OF EMBODIMENTS

Figure 2B:
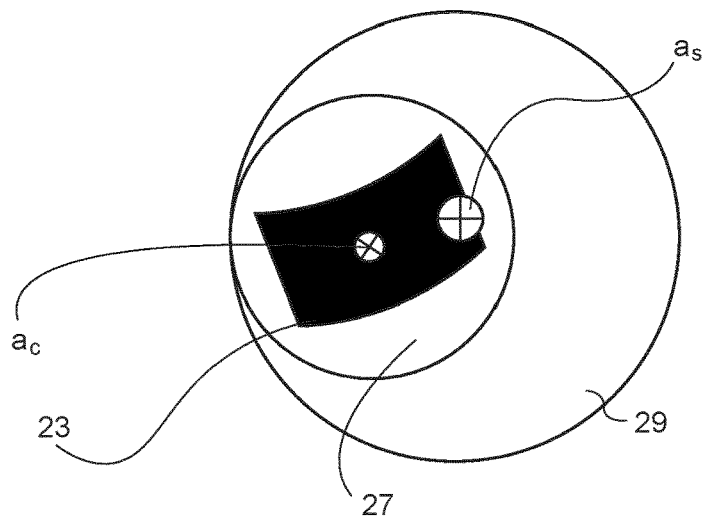

FIG. 1a illustrates a modulating assembly 10 according to embodiments of the invention. The modulating assembly includes a deflection device 11 arranged to deflect a beam emitted from a radiation source 13 in the vertical direction. Downstream of the deflection device 11, a modulator wheel 15 is arranged so as to be rotatable. The modulator wheel 15 is shaped as a rim of a circle or an ellipse having a varying thickness in the radial direction. A control system 17 is provided for controlling the function of the radiation source 13, the deflection device 11, the modulator wheel 15 and possibly other components of the modulating device. The control system 17 is arranged to ensure that the beam position and beam current are adapted to the rotation of the wheel. This may be done by modulating the beam current and the beam on intervals in synchronization with the rotation of the modulator wheel 15 by synchronizing the wheel with the beam current and position, or a combination of the two. The modulating device 10 is preferably enclosed in a box to protect the moving parts.

The thickness of the rotating wheel should vary so that the resulting energy of the ions after passing through the wheel will extend over the range needed to cover the target in the direction of the beam. The variation in thickness may be implemented in any suitable way. A simple and suitable way is shown in FIG. 1b, where the thickness decreases gradually over the 360 degrees from a maximum thickness to a minimum thickness. An alternative implementation is shown in FIG. 1c, in which the thickness increases in both directions from a minimum thickness to a maximum thickness in a position 180 degrees separated from the minimum thickness. As will be understood, the varying thickness can be configured in any suitable way, including random variation, as long as the wheel will affect the beam in the desired way. The exact thicknesses will, as the skilled person will realize, be adapted according to the energy of the emitted beam, the depth and extension of the target, the material of the wheel and other factors. The modulating assembly 10 may be used in combination with a rotation of the beam relative to the patient resulting in different beam angles. To achieve this, the patient may be seated on a support such as a chair that rotates or placed on a couch with a rotating gantry. Both these embodiments will be discussed below.

The wheel is arranged in the beam in a tilted or slanted position so that the beam deflected by the deflection device will pass through the rim of the wheel once. That way the beam will be affected by the thickness in each rotational position of the wheel over time as the wheel rotates. The beam may be arranged to pass from the inside of the wheel through the rim to the outside or from the outside to the inside.

Alternatively, the modulating wheel 15 can be positioned such that the beam will pass through the rim both from the outside in a first position, through the interior of the wheel and subsequently in a second position from the inside to the outside. In this case, the total thickness of the rim in both the first and the positions will affect the energy of the beam. The rotation of the wheel is much faster than the change of the beam angle, for example, 10 rounds per second.

The radiation source can be any suitable radiation source for providing the desired treatment, typically a horizontal static pencil beam having an energy of 200 MeV. The beam will be deflected in one direction by means of the deflection device. For some embodiments the deflection is in the vertical direction.

The deflection device may be any device suitable for deflecting the beam in at least one direction, such as a dipole magnet arranged to deflect the beam so that it will move along a vertical path over the patient outline over the area needed to cover the height of the target.

In addition to the components discussed above, the modulating device may comprise an aperture device 19 positioned downstream of the modulating wheel. This aperture device 19 may be any suitable static or dynamic aperture device and will serve to prevent the dose from spreading over a larger fraction of an organ at risk, which may serve to amplify the dose gap to valley ratio in an organ at risk while still enabling a near homogeneous dose in the target.

FIG. 2a discloses an embodiment of a radiation treatment system 20 including a modulating device 10 such as the one discussed in connection with FIGS. 1a, 1b and 1c. In this embodiment, a patient 21 to be treated is seated on a chair 23, which is mounted in such a way that it can rotate around its own axis $a_c$, as indicated by an arrow 25. Such rotating chairs are known in the art. A typical rotation speed is 1 round per minute. This way, since the rotation of the modulating wheel is much faster than the rotation of the chair, the beam will be modulated over the whole range of energy levels many times during the rotation of the patient. This modulation of the beam in combination with the slow rotation of the patient means that an ARC plan can be delivered to the patient without the delay conventionally caused by changing of energy levels. From the point of view of the radiation source, the arc treatment can be delivered as one uniform beam along a single vertical line. The deflection device, as explained above, deflects the beam in the vertical direction, so that the beam will cover a portion of the patient's body in the vertical direction.

FIG. 2b illustrates a development of the embodiment of FIG. 2a, in which the chair 23 is mounted on a base plate 27. Only the portion of the device comprising the chair is shown, as seen from above, to illustrate a relative movement of the chair 23 and the base plate 27. In the device shown in FIG. 2b, the chair 23 is mounted to be rotatable around its axis $a_c$ as in FIG. 2a. In addition the chair 23 is mounted on a base plate 27 that is mounted on the ground 29 in such a way that the base plate 27 is rotatable around a base axis $a_s$, which is displaced in the horizontal direction with respect to the chair's axis $a_c$. The base axis $a_s$ is also preferably eccentric with respect to the base plate. In this way, the simultaneous rotation of the chair and the base plate can generate more complex patterns of radiation inside the patient 21 because it allows the iso-center position to be changed during rotation of the patient. This is advantageous in particular for treatment of concave shapes, as illustrated in FIG. 2b.

Possible dimensions for the setup of FIGS. 2a and 2b may be, or example, 3 meters from the radiation source to the patient, with the deflecting device positioned 2.5 meters from the patient, for example as measured from the rotation axis $a_c$ of the chair. The deflection of the beam may be chosen so that the beam can cover 10 cm of the patient's surface in height. As will be understood, these dimensions are merely suggestions and the dimensions may be selected in any suitable way.

Treatment of a seated patient with a fixed beam line has a number of advantages. The apparatus is simpler and less expensive than a traditional couch and gantry apparatus. Simultaneously it may provide a better result in some cases, especially for treatment of the head and the thorax. Often, the patient will move less when sitting than when lying on a couch, which means that there will be less deviation from the actual plan.

Figure 3:
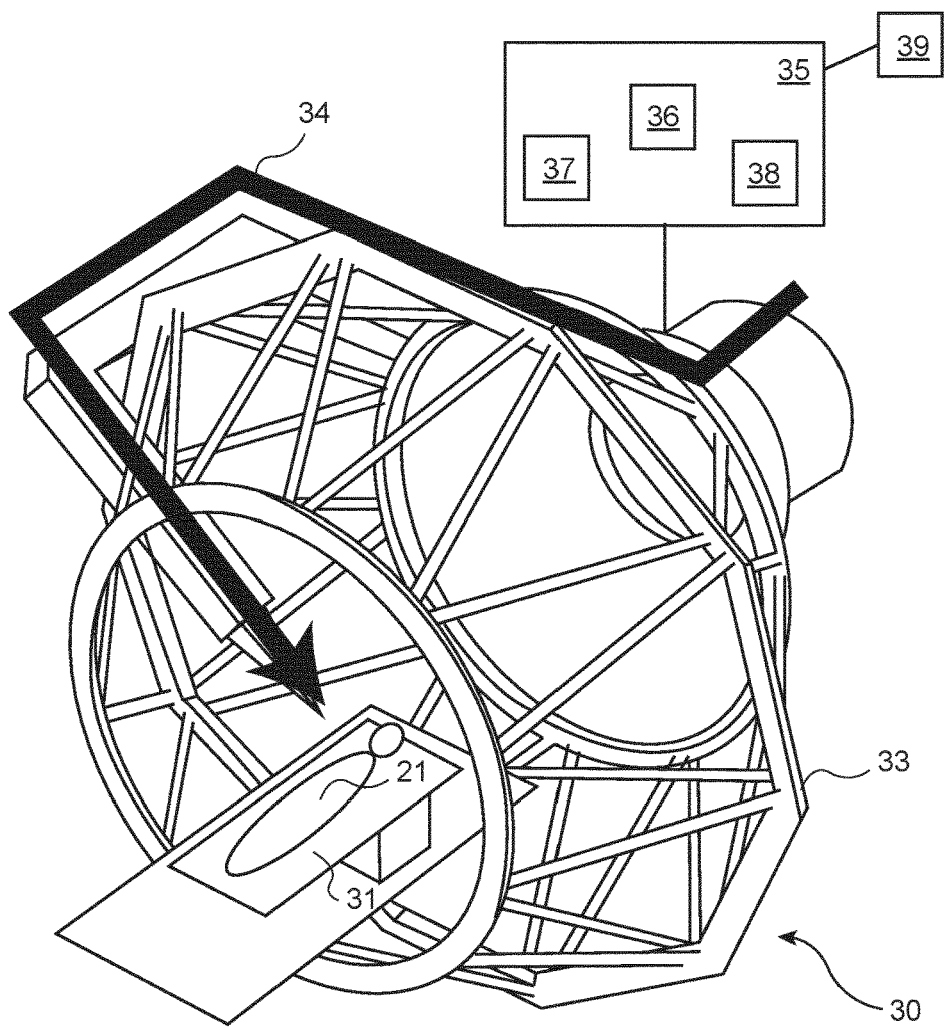

FIG. 3 discloses an alternative embodiment of a radiation treatment system 30 including a modulating assembly such as the one discussed in connection with FIGS. 1a, 1b and 1c. In this embodiment, a traditional setup with a couch 31 and proton gantry 33 is used, the gantry 33 being arranged to rotate around the couch 31 in the conventional way, while the patient 21 is lying on the couch. In this embodiment, however, the gantry 33 comprises a proton radiation source, and a modulating assembly 10 such as the one disclosed in connection with FIGS. 1a-1c. The solid arrow 34 indicates that path of one proton beam through the gantry. The scanning magnets that are usually found in a gantry may be used as the deflection device 11, or separate magnets may be provided. In this way, the radiation source 13 in the gantry 33 may emit one beam having a constant energy, and the energy may be modulated by the modulating wheel 15 in the same way as discussed in connection with FIG. 2a, the difference being that the relative rotation of the beam around the patient 21 is achieved by the rotation of the gantry 33 around the patient instead of the rotation of the patient relative to the incoming beam.

As is common in the art, the gantry is also controlled by a control unit 35 arranged to control the beam, the deflection device 11, the modulator wheel 1 and, if present, the compensator device 17. The control unit comprises a processor 36, and at one or more data memories 37 and program memories 38 and typically one or more input/output devices 39.

In all three setups described in connection with FIGS. 2a, 2b and 3, the beam may be emitted continuously during the rotation of the patient or the gantry, respectively, or at certain discrete chair or gantry angles. In the latter case, the angles may be spaced so that there are gaps of low dose between the neighboring chair angles, especially in organs at risk to achieve grid therapy effect.

Figure 4A:
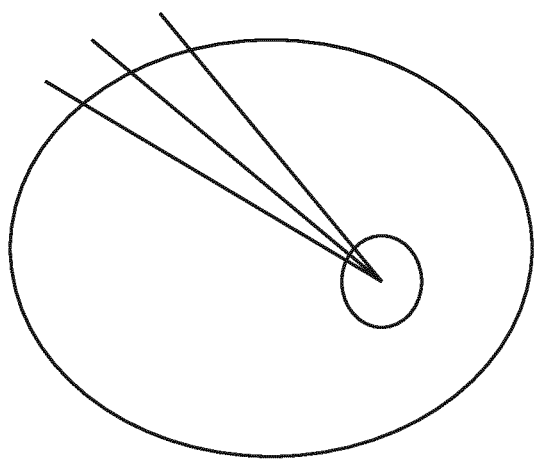
FIGS. 4a and 4b illustrate the intersection of beams with a patient in different embodiments of the radiotherapy treatment apparatuses according to FIGS. 2a, 2b and 3.

FIG. 4a illustrates an example of a beam pattern that may result from the setup of FIG. 2a or FIG. 3. A horizontal slice 41 through a patient is shown as seen from above. Beams 43 from three chair angles directed on a target volume 45 inside an organ at risk 47. Near the surface of the OAR the peak to value dose ration will increase. This will provide a grid therapy effect protecting OAR in the valley. If FLASH dose rates are used, the FLASH effect in the OAR will be enhanced in the peak region as the protons are concentrated there leading to increased dose rate.

Figure 4B:
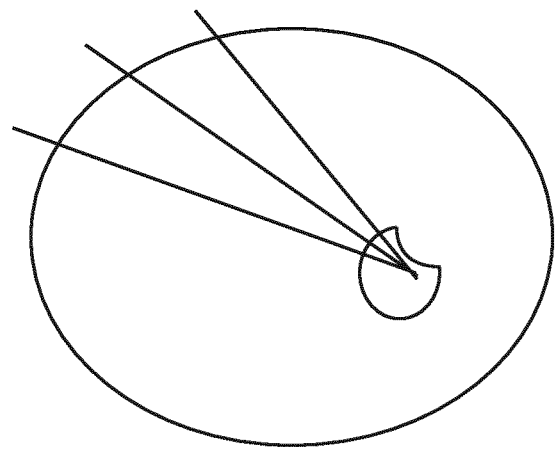

FIG. 4b illustrates an example of a beam pattern that may result from the setup of FIG. 2b. As in FIG. 4a, a horizontal slice 41 through a patient is shown as seen from above. Beams 43 from three chair angles directed on a target volume 45 inside an organ at risk 47. The combined rotational movements of the chair and the base plate mean that the area covered inside of the organ at risk can have a different shape than elliptic, in particular concave shapes can be covered.

Figure 5:
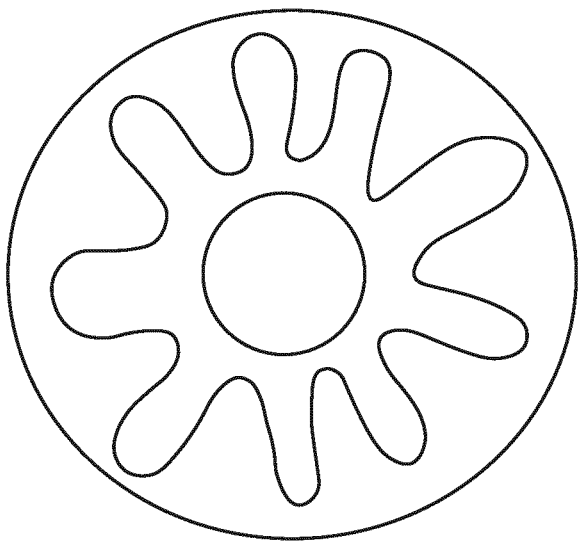
FIG. 5 illustrates a beam pattern that may result from an apparatus according to the embodiment of any one of FIGS. 2a, 2b and 3.

FIG. 5 shows an example of a resulting dose in a patient using the setup according to an embodiment of the invention and radiating from a number of beam angles, ten in the Figure. As can be seen, dose will be delivered to the patient in a number of beams, which will intersect in the target to provide the prescribed dose. Outside of the target, the beams will preferably not intersect, and there will be a region between each beam that will receive low or no dose, for example a dose between 10%-50% of the peak dose. Depending on the number of beams and the distance between them, this may provide a grid effect as discussed above. For achieving the FLASH effect, fewer beam angles should be used. This may result in a less homogeneous dose inside of the target.

Figure 6:
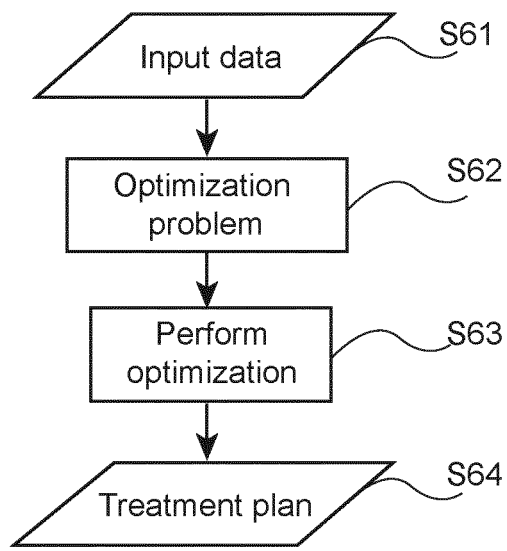
FIG. 6 is a flowchart of a method according to aspects of the invention.

FIG. 6 illustrates a general flowchart of a method that may be used for generating a treatment plan involving an apparatus as discussed above. Input data S61 includes a predicted dose distribution, In step S62, an optimization problem for the treatment plan is obtained, said optimization problem taking into account the model of the treatment apparatus involving a modulating device as discussed in connection with FIG. 1. In step S63, the optimization is performed to output a treatment plan S64 that will produce a dose as close as possible to the desired dose distribution.

The invention claimed is:

1. A radiation delivery apparatus (20;30) comprising a radiation modulating assembly (10) comprising a modulator wheel (15), said modulator wheel being shaped as a rim defining the circumference of a circle or an elliptic shape, and having varying thickness around the circumference, said modulator wheel (15) being arranged in such a way that a beam traveling from a radiation source (13) to a patient will intersect the rim of the modulator wheel, said wheel being arranged to rotate in such a way that the beam will intersect the rim in varying positions around the circumference, said apparatus further comprising a support (23;31) arranged to hold a patient during treatment, wherein the support is a chair (23) in which the patient (21) may be seated during treatment, said chair being arranged to rotate around a first axis (ac) so that during treatment the beam will enter the patient from different angles in a horizontal plane.

2. A radiation delivery apparatus according to claim 1, wherein the radiation modulating assembly (10) further comprises a deflecting device (11) arranged upstream of the modulator wheel (15), said deflecting device (11) being arranged to deflect the beam in at least one dimension, in such a way that the deflected beam will intersect the rim of the modulator wheel (15).

3. A radiation delivery apparatus according to claim 2, wherein the modulator wheel (15) is arranged with a slanted orientation relative to the deflecting device (11), in such a way that a beam after passing through the deflecting device (11) will intersect the rim once.

4. A radiation delivery apparatus according to claim 2, further comprising a radiation source (13) arranged to provide a beam in such a direction that it will be deflected by the deflecting device (11) and pass through the modulator wheel (15).

5. A radiation delivery apparatus according to claim 2, wherein the deflecting device (11) comprises a device arranged to create a magnetic field to deflect the beam.

6. A radiation delivery apparatus according to claim 1, wherein the radiation modulating assembly (10) further comprises an aperture device (19) downstream of the modulator wheel (15).

7. A radiation delivery apparatus according to claim 1, wherein the deflecting device (11) comprises a single magnet with a narrow pole gap.

8. A radiation delivery apparatus according to claim 1, wherein the deflecting device (11) is arranged to move the beam in a direction having a component perpendicular to the direction of rotation, preferably perpendicularly to the direction of the rotation.

9. A radiation delivery apparatus according to claim 1, wherein the chair (23) is rotatably mounted on a rotatable base plate (25) arranged to rotate around a second axis (as) during treatment, wherein the chair is mounted so that the first axis (ac) is spaced apart from the second axis (as).

10. A radiation delivery apparatus according to claim 1, wherein the chair (23) is rotatably mounted and arranged to be linearly displaced along a first and a second axis during treatment.

11. A radiation delivery apparatus according to claim 1, wherein the support is a couch (31), the device comprising a gantry, wherein the gantry includes the radiation source and the deflecting device.

* * * * *